United States Patent [19]
Van Hale

[11] Patent Number: 5,554,026
[45] Date of Patent: Sep. 10, 1996

[54] DENTAL HAND PIECE

[76] Inventor: Gregory L. Van Hale, 247 W. Glenoaks, Glendale, Calif. 91202

[21] Appl. No.: 296,249

[22] Filed: Aug. 25, 1994

Related U.S. Application Data

[63] Continuation-in-part of Ser. No. 24,375, Mar. 1, 1993, Pat. No. 5,342,196.

[51] Int. Cl.⁶ ............................ A61C 17/02; A61C 17/06
[52] U.S. Cl. ............................... 433/82; 433/91; 433/132
[58] Field of Search ......................... 433/132, 91, 114, 433/115, 116, 126, 82; 415/904

[56] References Cited

U.S. PATENT DOCUMENTS

| | | | |
|---|---|---|---|
| 2,884,695 | 5/1959 | Ellis | 433/132 |
| 3,120,705 | 2/1964 | Hoffmeister et al. | 433/130 |
| 3,512,258 | 5/1970 | Johnson | 433/91 |
| 3,646,678 | 3/1972 | McAlister | 433/91 |
| 3,768,477 | 10/1973 | Anders et al. | 433/91 |
| 4,176,453 | 12/1979 | Abbott | 433/91 |
| 4,253,831 | 3/1981 | Eaton, II | 433/91 |
| 5,122,153 | 6/1992 | Harrel | 433/91 |
| 5,252,067 | 10/1993 | Kakimoto | 433/132 |

*Primary Examiner*—Cary E. O'Connor
*Attorney, Agent, or Firm*—J. E. Brunton

[57] ABSTRACT

An aspirating dental hand piece having at its distal end a vacuum scoop that circumscribes the work tool and automatically carries away cooling water and debris during operation of the hand piece. The hand piece includes a two-part handle. The distal portion of the handle terminates in a suction scoop or shroud within which the gas driven motor is housed. This portion of the handle is divided into two portions, one of which houses the cooling fluid, gas and fiber optic conduits, and the other of which forms a fluid passageway in communication with the suction scoop for carrying away the cooling fluid and the debris generated during the drilling and grinding operations. The fluid and debris passageway is sealed with respect to the conduit carrying portion of the handle.

18 Claims, 8 Drawing Sheets

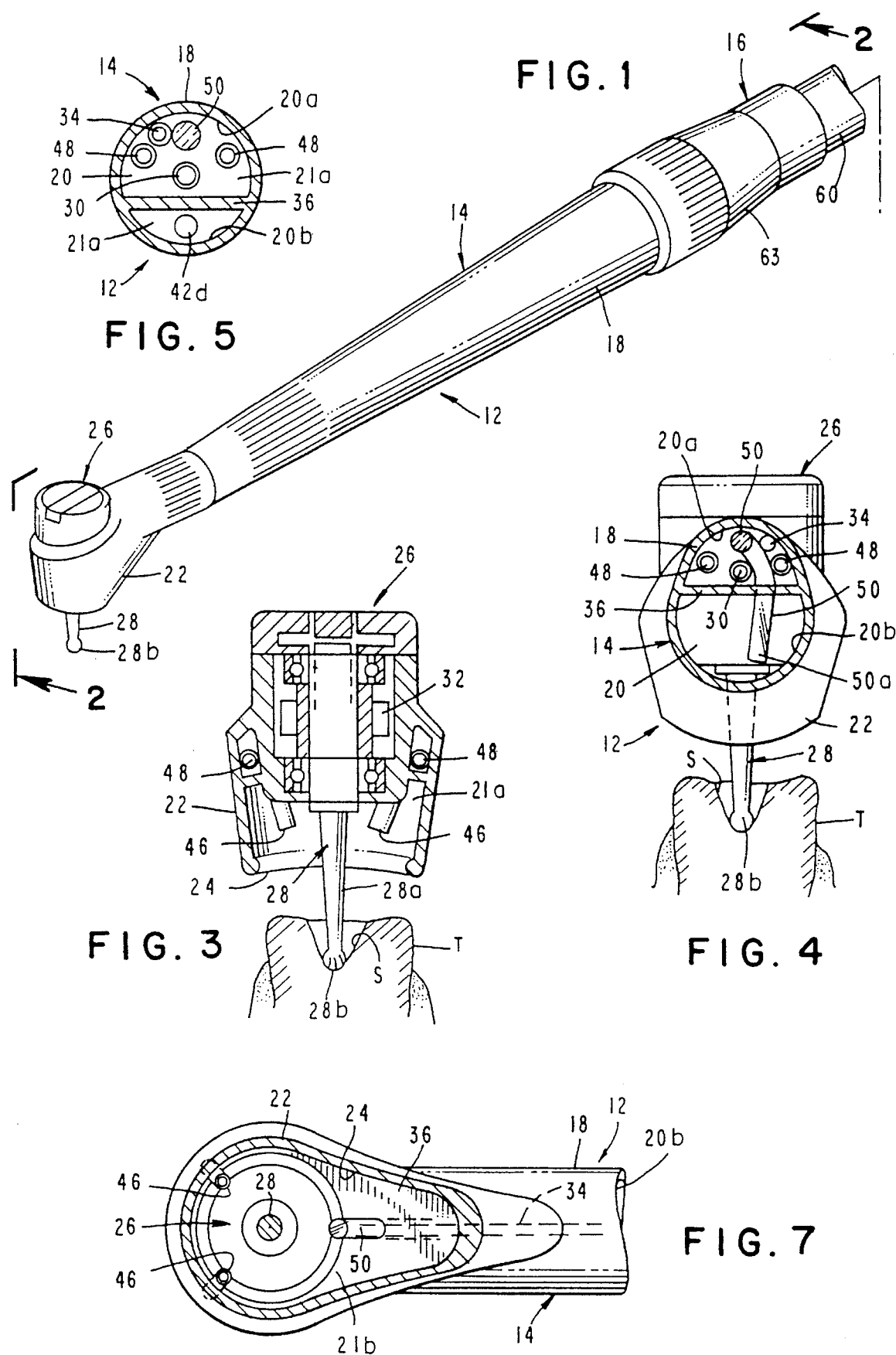

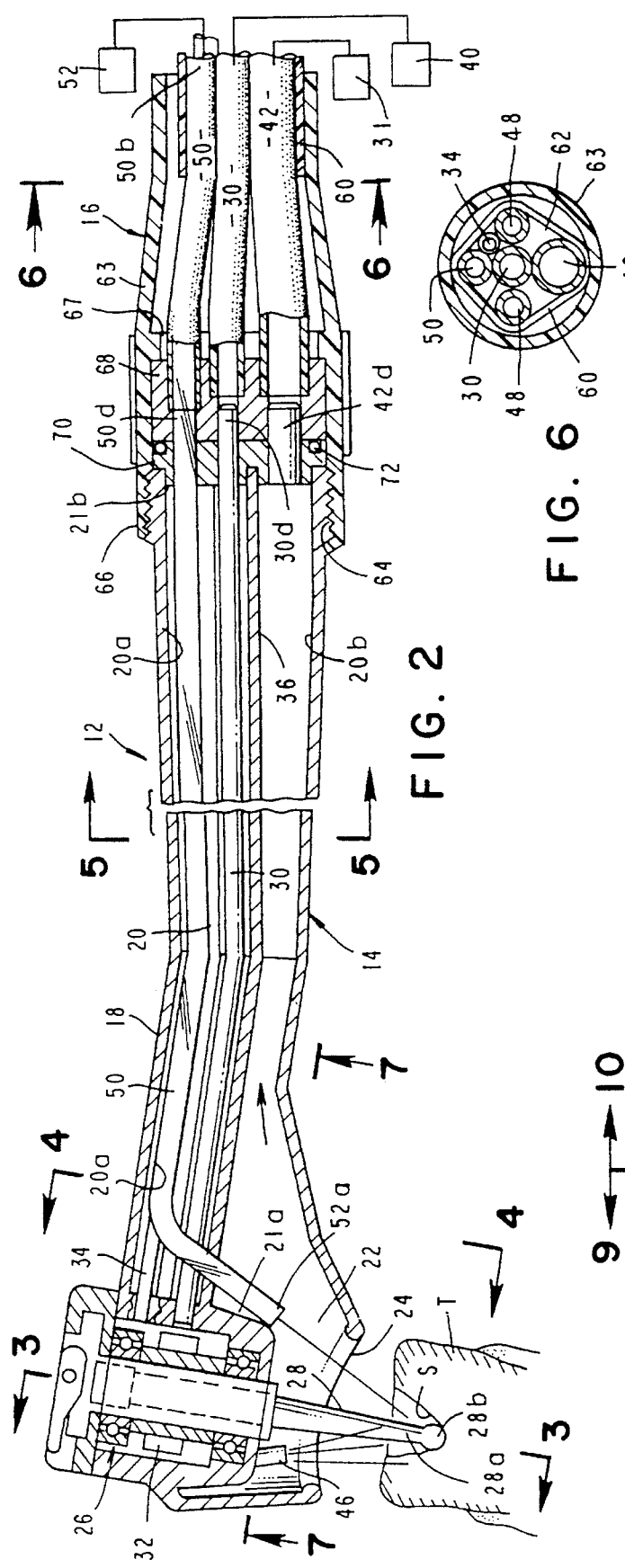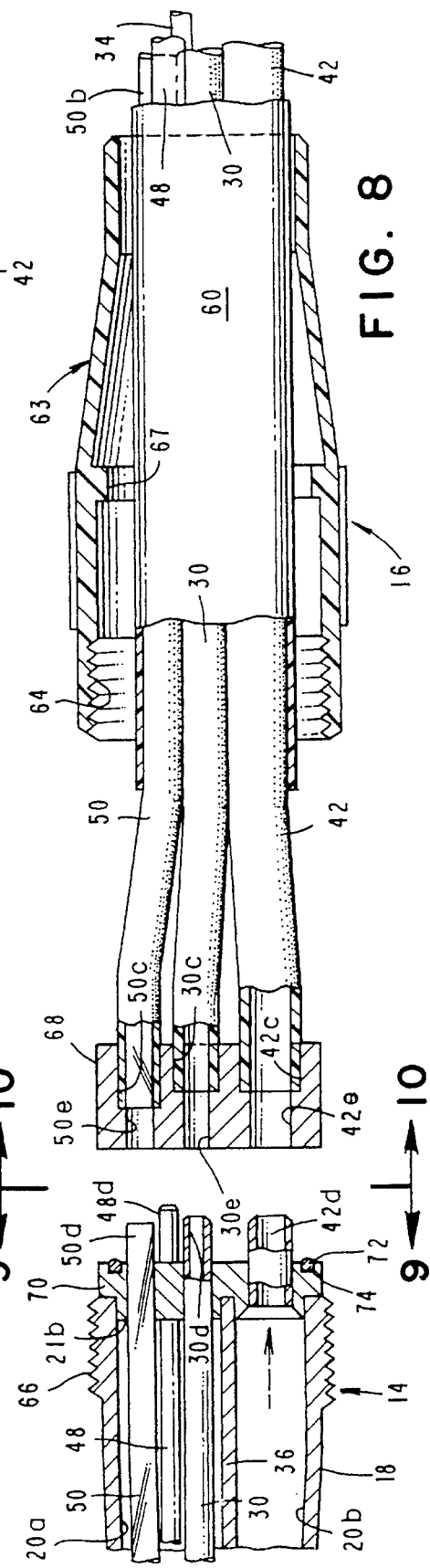

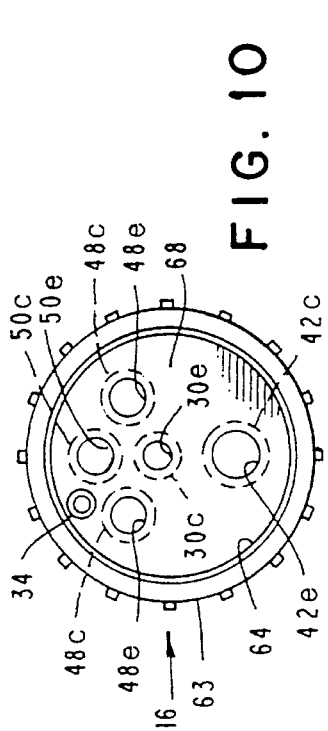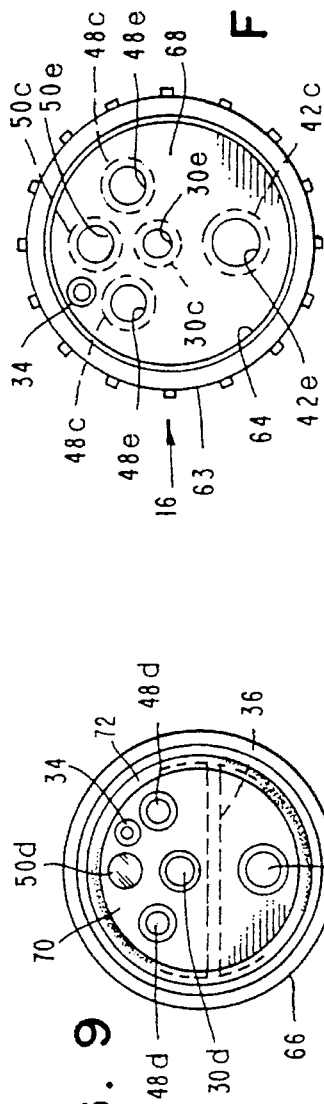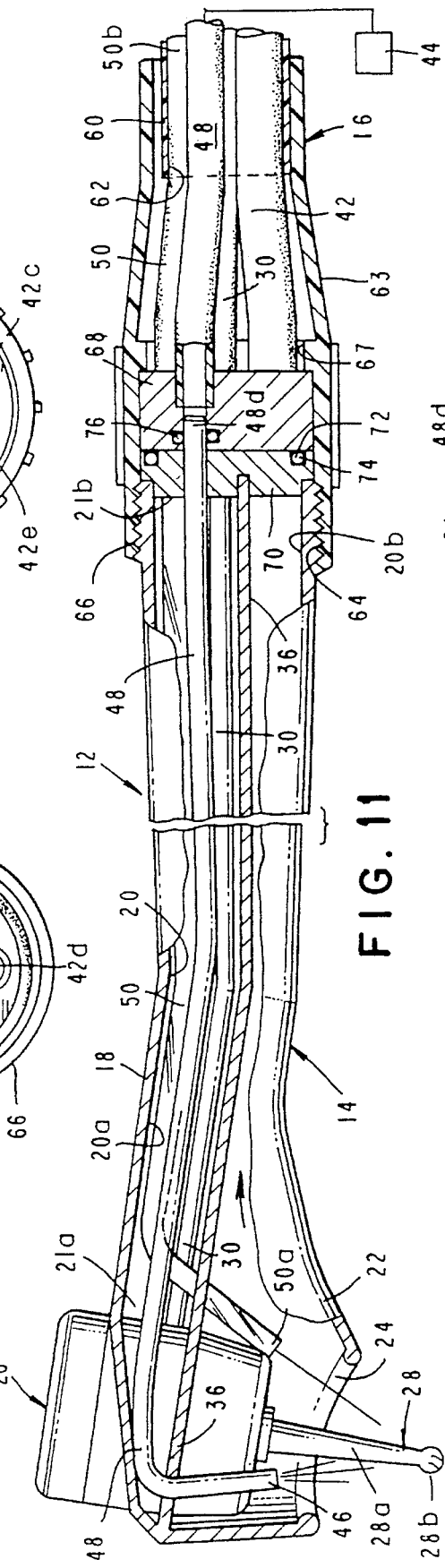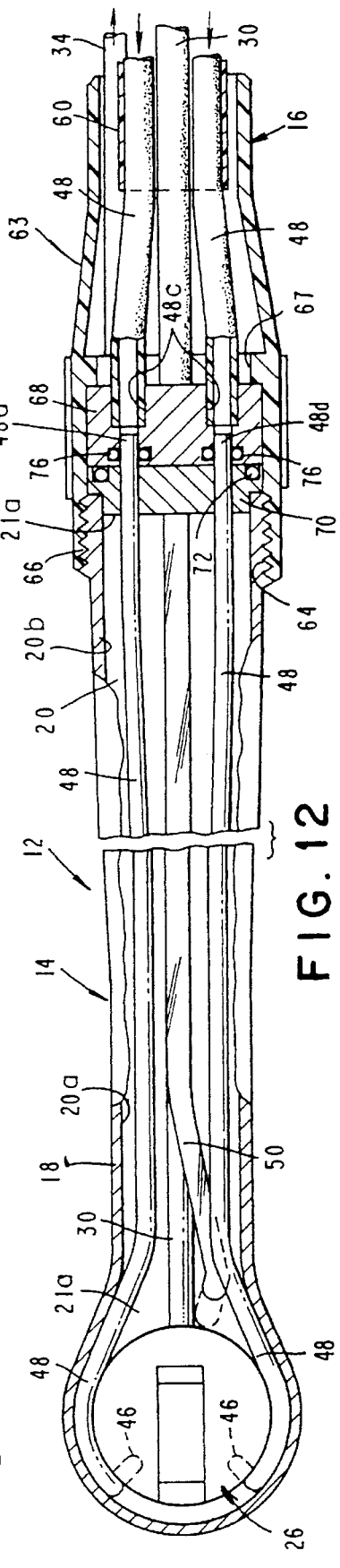

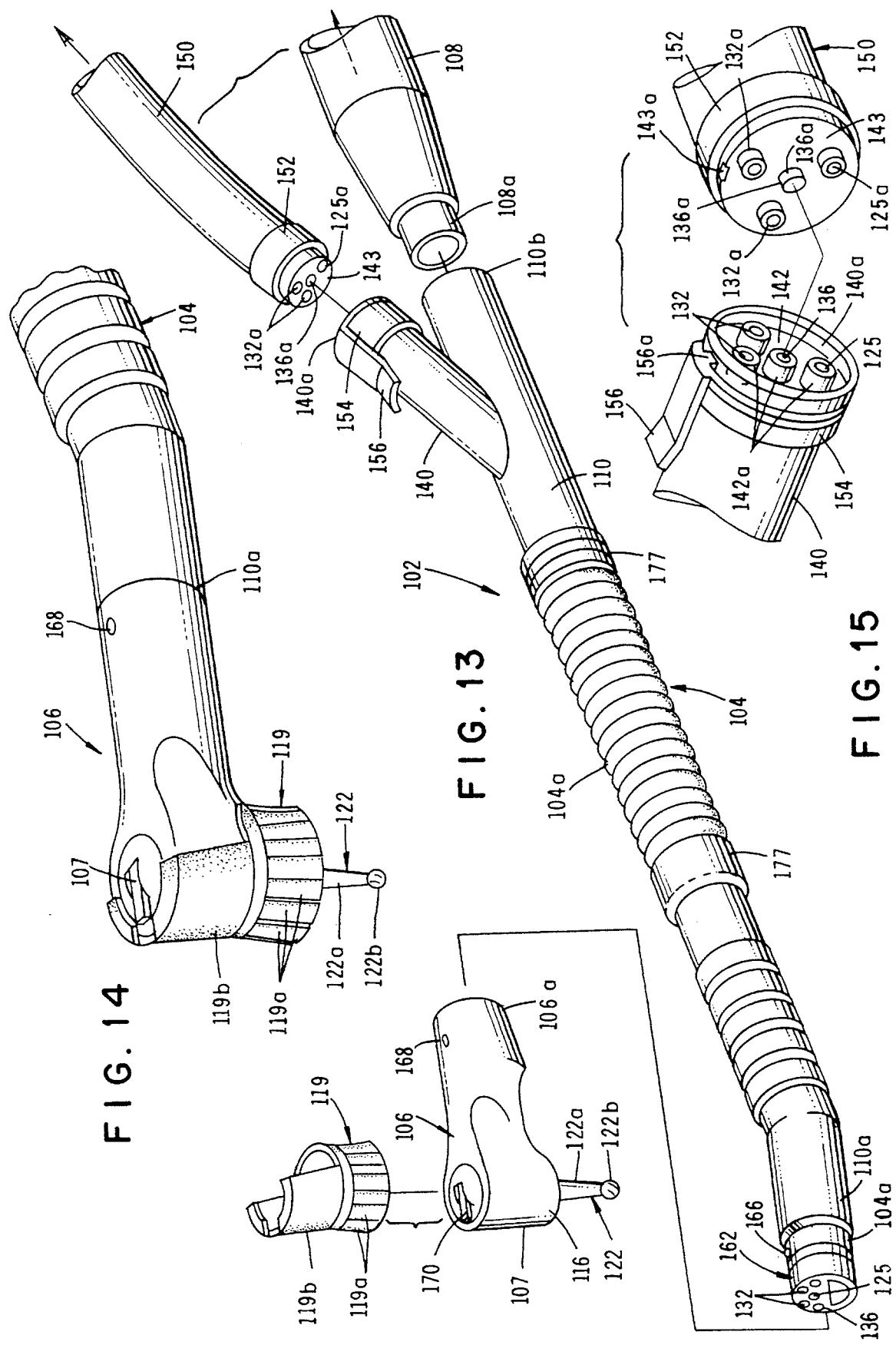

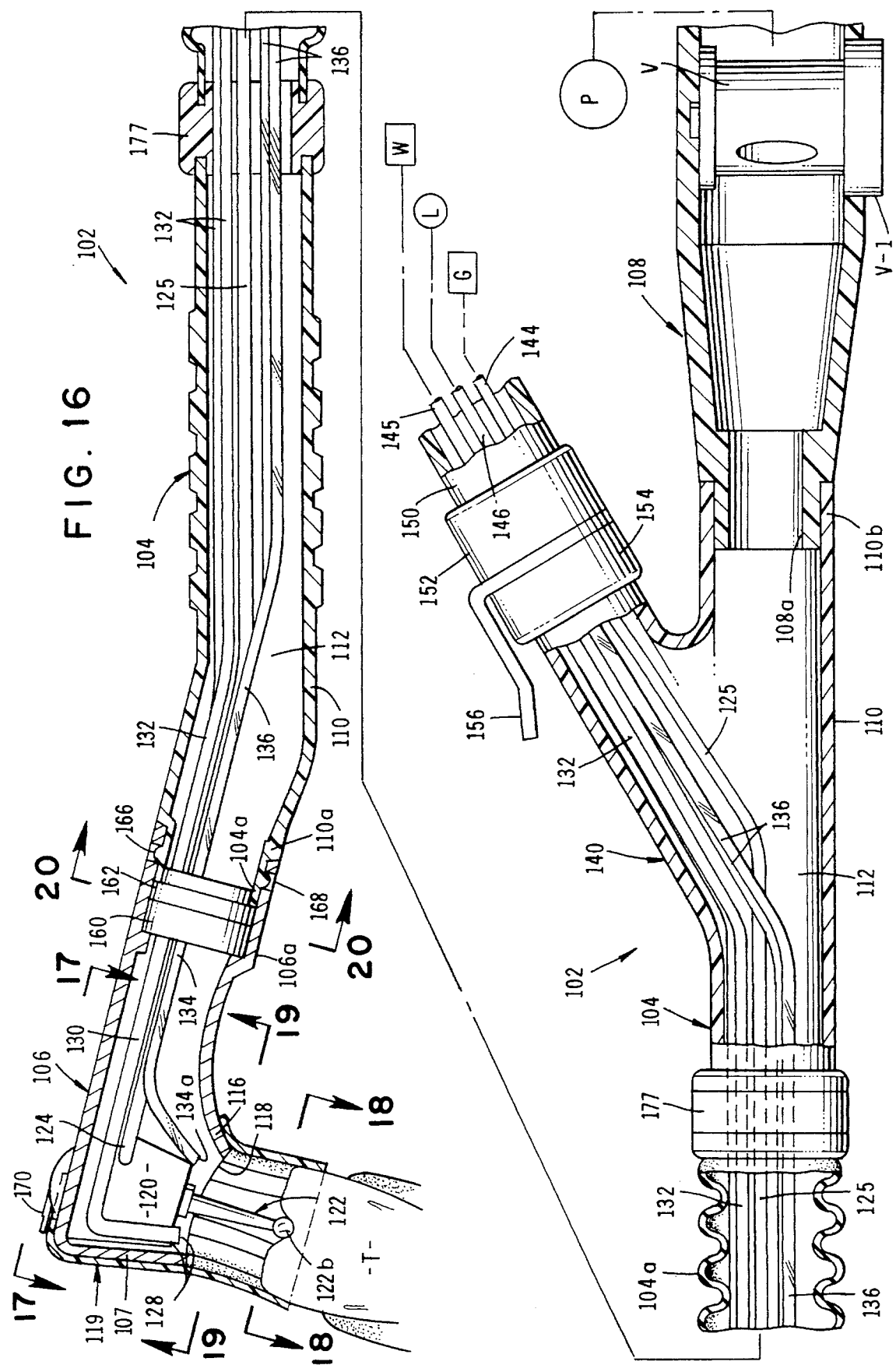

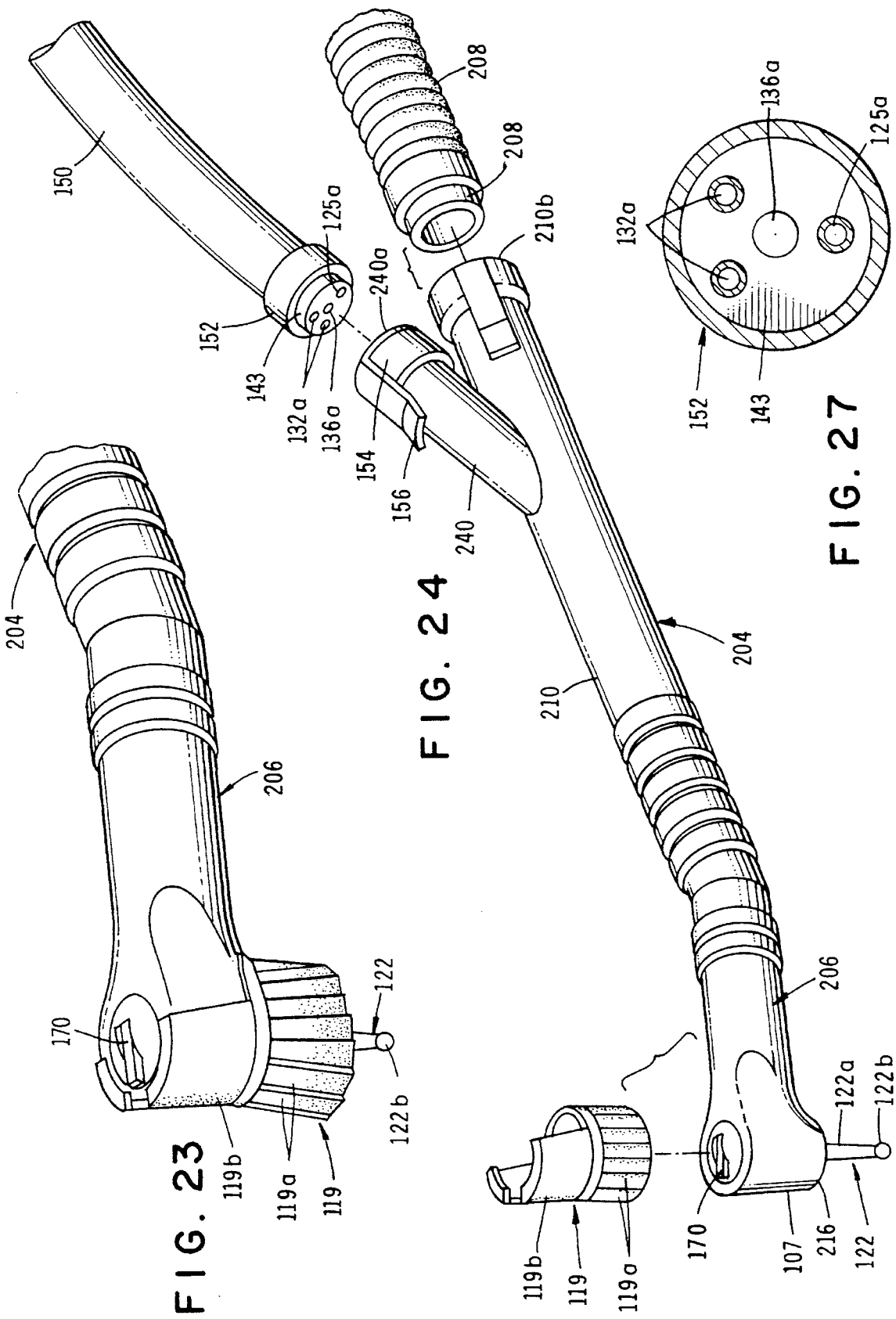

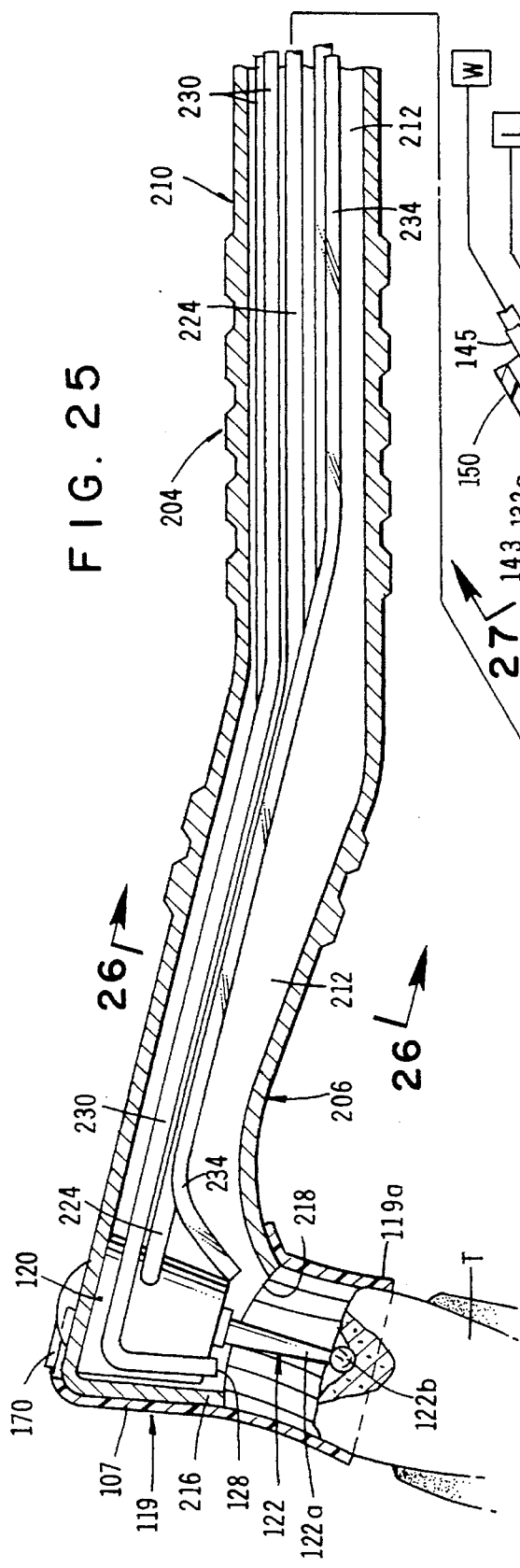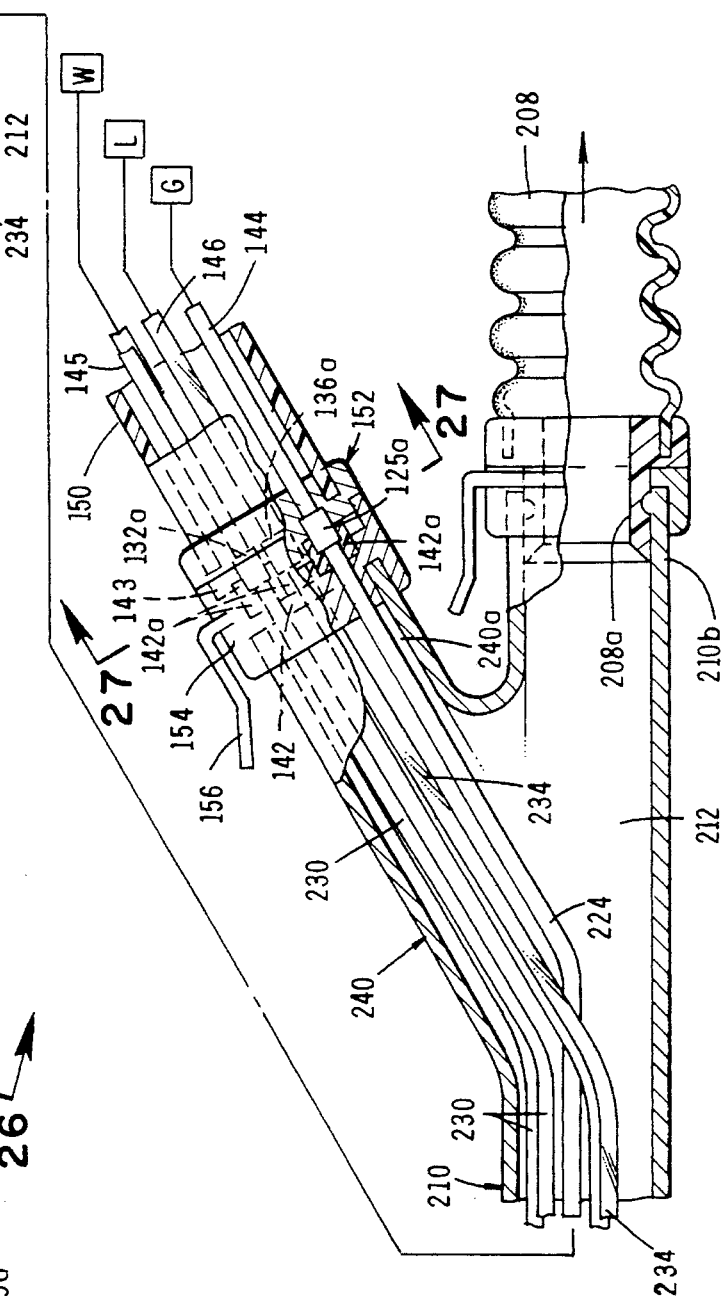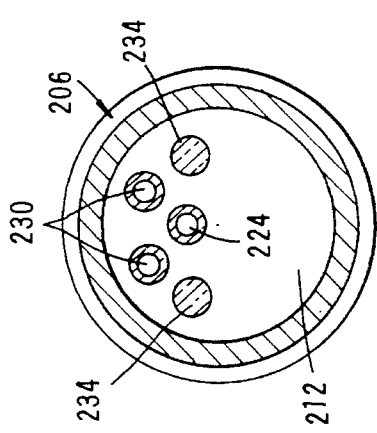

DENTAL HAND PIECE

This is a Continuation-In-Part application of U.S. application Ser. No. 08/024,375 filed Mar. 1, 1993, now U.S. Pat. No. 5,342,196.

BACKGROUND OF THE INVENTION

1. Field of the Invention

The present invention relates generally to dental hand pieces. More particularly, the invention concerns an aspirating dental hand piece having at its distal end a vacuum scoop that circumscribes the work tool and automatically carries away cooling water and debris during operation of the hand piece.

2. Discussion of the Invention

High speed gas driven dental hand pieces are well known in the prior art. Typically such hand pieces include a gas driven motor provided at the distal end of a handle for driving a work tool at high speeds of rotation. During operation of the hand piece, it is necessary to direct a cooling fluid toward the work tool to cool it and the work site and to wash away tooth debris formed during performance of the dental procedure.

In the past, separate aspiration or suction devices have been used to collect the cooling fluid and debris and carry it away from the work site. Generally these devices include an elongated tube having a suction nozzle at one end which is disposed within the patient's mouth proximate the tooth being worked on. These suction devices are generally unwieldy and must be operated by the dental assistant as the dentist performs the dental procedure using the dental hand piece. Accordingly, two people, that is the dentist and the dental assistant, must both be present during the dental procedure.

The present invention overcomes this significant drawback by providing as an integral part of the dental hand piece itself, a suction means for automatically carrying away the cooling water and the dental debris generated during the performance of the dental procedure. Since the dentist is manipulating the hand piece along with the built-in suction means, the dental assistant is not needed and can be performing other important work such as sterilization in accordance with recent OSHA procedures.

The hand piece of one form of the present invention includes a two-part handle. The distal portion of the handle terminates in a suction scoop or shroud within which the gas driven motor is housed. This portion of the handle is uniquely divided into two portions, one of which houses the cooling fluid, gas and fiber optic conduits, and the other of which forms a fluid passageway in communication with the suction scoop for carrying away the cooling fluid and the debris generated during the drilling and grinding operations. Due to the unique design of the suction means of the invention, greater amounts of water than normal can be used to ease the cutting process. The fluid and debris passageway is sealed with respect to the conduit carrying portion of the handle. The proximal portion of the handle, which is removably interconnected with the distal portion by appropriate coupling means, carries the cooling fluid, gas, vacuum and fiber optic input conduits which are, in turn, interconnectable with the conduits carried by the distal portion of the handle upon mutably interconnecting the two portions of the handle.

U.S. Pat. No. 4,203,221 issued to Knop et al discloses a two part dental hand piece and includes resilient means forming a portion of the means for interconnecting the two parts of the handle. This patent nowhere discloses or suggests the novel suction means of the apparatus of the present invention.

U.S. Patent No. 4,249,896 issued to Kerfoot, Jr. discloses a gas driving dental hand piece having decreased noise and improved vibration damping characteristics. Kerfoot also fails to disclose or suggest any type of integral vacuum system of the character disclosed herein.

SUMMARY OF THE INVENTION

It is an object of the present invention to provide a dental hand piece which includes an integral suction system for automatically carrying away from the work site cooling water and debris generated during the performance of the dental procedure.

More particularly, it is an object of the invention to provide a dental hand piece of the aforementioned character in which the gas driven motor which drives the work tool is housed within a downwardly depending shroud that uniquely functions as a suction scoop for automatically capturing the cooling water which cools the work site and the debris, including tooth debris, saliva, blood and lake materials which are formed during drilling and grinding of the patient's tooth.

Another object of the invention is to provide a dental hand piece and integral suction system which can be operated by the dentist using one hand without the aid of a dental assistant thereby decreasing the number of people exposed to any pathogens encountered during the operating procedure.

Another object of the invention is to provide a device of the character described in the preceding paragraphs which includes built-in illumination means for illuminating the work area.

Another object of the invention is to provide a hand piece as described which is compact, light weight, easy to use and easy to clean and sterilize.

Still another object of the invention is to provide a combined hand piece and suction unit which includes readily interconnectable distal and proximal portions, the distal portion being divided into two portions one of which comprises a fluid passageway for carrying away the cooling fluid and the dental debris.

Yet another object of the invention is to provide a dental hand piece of the class described that is compatible with standard sources of compressed gas, vacuum and electrical power.

Another object of the invention is to provide an apparatus as described which decreases the amount of airborne particles, aerosols and other contaminates which may be generated during the operating procedure.

Another object of the invention is to provide a dental hand piece of the character described in the preceding paragraphs which is of simple design for ease of manufacture and one which can be inexpensively produced in large volume.

Still another object of the invention is to provide a dental hand piece having a plastic central-body portion which is disposable and is removably attached proximate one end to a source of vacuum and is removable attached proximate its other end to a motor housing having a suction scoop of novel design which efficiently captures the cooling water and the debris generated by the work tool.

BRIEF DESCRIPTION OF THE DRAWINGS

FIG. 1 is a generally perspective view of one form of the aspirating hand piece of the invention.

FIG. 2 is a cross-sectional view taken along lines 2—2 of FIG. 1.

FIG. 3 is a cross-sectional view taken along lines 3—3 of FIG. 2.

FIG. 4 is a cross-sectional view taken along lines 4—4 of FIG. 2.

FIG. 5 is a cross-sectional view taken along lines 5—5 of FIG. 2.

FIG. 6 is a cross-sectional view taken along lines 6—6 of FIG. 2.

FIG. 7 is a view taken along lines 7—7 of FIG. 2.

FIG. 8 is an exploded side elevational, cross-sectional view similar to FIG. 2 but showing the rearward portion of the apparatus separated from the forward operating portion.

FIG. 9 is a view taken along lines 9—9 of FIG. 8.

FIG. 10 is a cross-sectional view taken along lines 10—10 of FIG. 8.

FIG. 11 is a side elevational view similar to FIG. 2 showing the routing of the cooling water conduit.

FIG. 12 is a top cross-sectional view further illustrating the routing of the cooling water conduit and the light conducting fiber optic conduit.

FIG. 13 is a generally perspective exploded view of an alternate form of the aspirating hand piece of the invention which includes a disposable central handle portion of novel design.

FIG. 14 is an enlarged, generally perspective view of the forward, working tool supporting portion of the hand piece which is removably affixed to the disposable central handle portion of the hand piece.

FIG. 15 is a fragmentary, exploded perspective view of the connector unit of the hand piece for interconnecting the gas and water supply, as well as the optical fiber bundles of the forward portion, with the disposable handle portion.

FIG. 16 is a side-elevational, cross-sectional view of the hand piece assembly shown in FIG. 13.

FIG. 23 is a generally perspective view of the forward portion of still another form of the aspirating hand piece of the invention.

FIG. 24 is a generally perspective, exploded view of the alternate embodiment of the invention.

FIG. 25 is a side-elevational, cross-sectional view of the apparatus of this latest form of the invention.

FIG. 26 is a cross-sectional view taken along lines 26—26 of FIG. 25.

FIG. 27 is a cross-sectional view taken along lines 27—27 of FIG. 25.

DESCRIPTION OF THE INVENTION

Figure 17:
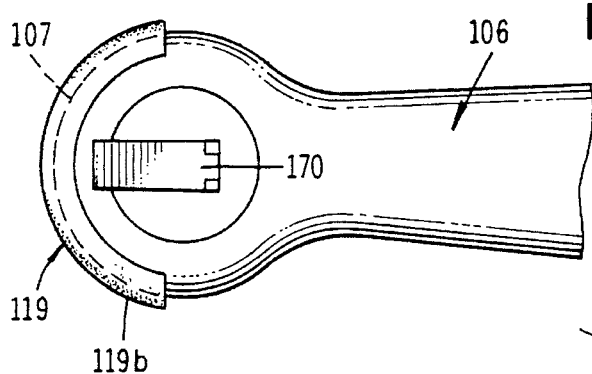
FIG. 17 is a cross-sectional view taken along lines 17—17 of FIG. 16.

Referring to the drawings and particularly to FIGS. 1 and 2, the aspirating dental hand piece system of one form of the present invention comprises an elongated handle assembly 12 made up of first and second releasably interconnected handle members 14 and 16 which are constructed of a suitable metal such as stainless steel or the like. First handle member 14 includes an outer wall 18 defining an interior space 20 having first and second ends 20a and 20b. First or distal end 20a terminates in intake means shown here as a downwardly depending shroud or scoop-like portion 22 having an open mouth 24. A gas driven motor 26 is carried at the distal end of handle member 14 and is adapted to rotatably drive a work tool 28 at very high speeds of rotation. Gas driven motor 26 is driven in conventional fashion by a gas under pressure such as air carried by a gas conduit 30 which is interconnected with a source of compressed gas 31. Motor 26 is of a conventional design well known to those skilled in the art and readily available from a number of manufacturers including KaVo America Corporation of Hoffman Estates, Ill. Work tool 28 is driven by the gas turbine portion 32 of gas motor 26 with exhaust gases being carried away from the turbine by an exhaust conduit 34 which extends through the handle assembly and appropriately exhausts to atmosphere at the proximal end of the handle assembly. Work tool 28 includes an elongated shank 28a which extends from mouth 24 and terminates in a grinding burr 28b.

Referring to FIG. 5, an important feature of the present invention resides in the provision of a transversely-extending interior dividing wall 36 which is connected to outer wall 18 internally of handle member 14. Wall 36 uniquely divides interior space 20 into upper and lower, or first and second, portions designated in FIG. 5 by the numerals 20a and 20b. As best seen in FIG. 2, portion 20b of the interior space is operably interconnected with vacuum means including a vacuum source such as vacuum pump 40 of standard construction. Pump 40, which is interconnected with space 20b by means of an elongated conduit 42, is adapted to create a vacuum within chamber 20b that is sufficient to capture and channel into interior portion 20b cooling water and debris generated during the grinding and drilling of the patient's tooth T.

In order to cool the work tool 28 and the work site S formed in tooth T, fluid cooling means are provided. The fluid cooling means here comprises a source of cooling fluid 44 (FIG. 11), which is preferably cool water. A pair of fluid spray jets 46 are mounted within shroud portion 22 for controllably directing the cooling water toward the work tool and the work site S. Also comprising a part of the cooling means are water carrying conduits 48 (FIG. 12) which extend through the handle assembly and function to appropriately interconnect the source of cooling water with spray jets 46 which are mounted distally with respect to work tool 28.

In the embodiment of the invention shown in the drawings, there is also provided illumination means for illuminating the work tool and the work site. The illumination means is here provided in the form of a multiplicity of optic fibers contained within an optic fiber conduit 50, one end 50a of which is disposed proximate mouth 24 of shroud 22 and the other end 50b of which is interconnected with a suitable source of illumination such as a light 52 (FIG. 2). Both the source of light and the fiber optic conduits are of a character well known to those skilled in the art.

An important feature of the apparatus of the present invention resides in the fact that the compressed gas conduits, cooling water conduits, and the optic fiber conduits and the exhaust conduit are all disposed within the sealed upper interior space 20a of the distal end piece member 14

(FIG. 4). Because all of the utility conduits are housed within the upper interior space 20a of the distal handle member, interior space 20b of the handle is free and open so as to efficiently conduct away from the work site excess cooling water and grinding debris resulting from the dental procedure. Since the upper and lower interior spaces 20a and 20b are separated by divider wall 36, the fiber optic gas, and cooling water conduits are protected from contamination which might be caused by the cooling water and debris flowing through space 20b of the forward hand piece member 14.

Turning now to FIGS. 6 through 12, second handle member 16 includes an outer wall 60 which defines an interior space 62. Slidably mounted over Wall 60 is a connector ring 63 which is provided with internal threads 64 disposed proximate its inboard end. Threads 64 are adapted to mate with external threads 66 provided on first handle portion 14. Threads 66 along with ring 63 comprise the connector means of the present form of the invention for interconnecting the first and second handle members 14 and 16. As best seen by referring to FIG. 6, the various utility conduits which carry the cooling water, vacuum compressed gas and fiber optics are all contained within internal space 62 and extend therefrom at the proximal end of the handle assembly for appropriate interconnection with the various sources of supply (FIGS. 2 and 11).

As best seen in FIGS. 11 and 12, disposed internally of ring 63 is an end wall 68 which sealably abuts an end wall 70 which closes interior space 20a and 20b of the first handle member 14. When threads 64 and 66 are mated an internal step 67 provided within ring 63 urges walls 68 and 70 into close proximity. An elastomeric O ring 72 which is disposed in an O ring groove 74 provided in end wall 70 prevents fluid leakage between the walls. As best seen by also referring to FIGS. 8 and 10, each of the utility conduits 30, 42 and 50 are received within spaced-apart bores 30c, 42c and 50c provided in end wall 68. In the manner shown in FIG. 8. Similarly, as indicated in FIG. 12, fluid conduits 48 are received within spaced-apart bores 48c provided in wall 68. As depicted in FIGS. 8 and 10, portions 30d, 42d, 48d and 50d respectively of the utility conduits 30, 42, 46 and 50 extend through wall 70 so that the end portions thereof can be received within reduced diameter bores 30e, 42e, 48e and 50e respectively provided in wall 68 which bores communicate with the utility conduits 30, 42, 48 and 50. As indicated in FIG. 12, elastomeric O rings 74 which are carried in O ring grooves provided in end wall 68 sealably engage end portions 48d of fluid conduits 48 so as to prevent fluid leakage between the conduits and end wall 68. With the construction thus described, when handle members 14 and 16 are interconnected by ring 63, the various utility conduits mate in the manner shown in the drawings to provide fluid flow paths between the utility sources and the distal portion of the handle assembly. It is apparent that by rotation of ring 63, the distal and proximal portions of the handle assembly can be quickly and easily disconnected so that the distal or forward portion of the handle assembly can be appropriately cleaned, and maintained.

In using the aspirating dental hand piece system of the form of the invention shown in FIGS. 1 through 12, the distal and proximal portions of the handle assembly are first threadably interconnected in the manner shown in FIG. 2. This renders the hand piece operable and the gas motor 26, the illumination means and the vacuum pump can be energized. Upon starting the flow of the cooling water, the device is used in a standard manner to perform the dental procedure. However, because of the unique design of the device, it is apparent that, when the device is in the position shown in FIG. 2, the vacuum source will create a sufficient negative pressure at the mouth 24 and within passageway 22 to cause the cooling water and the dental debris generated by the work tool to be sucked into mouth 24 and thence rearwardly of the distal hand piece and through interior space 20b of the distal portion of the hand piece to a suitable receptacle. The unique design of shroud 22 and open mouth 24 insures that during normal grinding and drilling procedures the cooling water and debris will automatically be removed from the work site without the need for auxiliary suction devices of the character normally operated by the dental assistant.

Referring now to FIGS. 13 through 16, another form of aspirating hand piece of the invention is there shown. This embodiment is similar in some respects to the previously described embodiment, but uniquely comprises an elongated handle assembly 102 the central portion 104 of which is disposable. Removably connected to disposable portion 104 proximate one end thereof is an intake means, which includes a housing 106, and releasably connected thereto proximate the other end is a vacuum supply means, including a tubular supply conduit 108.

Central portion 104 is preferably constructed of a flexible plastic tubular material and includes an outer wall 110 having first and second ends 110a and 110b. As best seen in FIG. 16, wall 110 defines a longitudinally extending interior space 112 (FIG. 16). First, or distal end 110a carries interconnection means, the character of which will presently be described, for connecting housing 106 to central handle portion 104. Second end 110b of wall 110 terminates in a tubular portion which is adapted to telescopically receive a reduced diameter portion 108a of vacuum supply 108.

Turning particularly to FIGS. 14 and 16, it can be seen that housing 106 terminates proximate its forward end in a downwardly depending scoop-like portion 116 having an open mouth 118. A gas driven motor 120, which is carried within housing 106, is adapted to rotatably drive the work tool 122 which extends outwardly from mouth 118 for engagement with the work site such as a tooth "T". Motor 120 is driven in conventional fashion by a compressed gas, such as compressed air. The compressed air is carried to the motor by a gas conduit 124 which is in communication with a remotely located source of compressed gas "G" (FIG. 16). Motor 120 is of a conventional design well known to those skilled in the art and readily available from a number of manufacturers including KaVo America Corporation of Hoffman Estates, Ill. Work tool 122 is driving at very high rates of speed by the gas turbine portion of the gas motor and includes an elongated shank 122a which terminates in a grinding burr 122b. Motor 120 exhausts directly into space 112 and aids aspiration via a venturi effect.

An important feature of the present invention is the specially configured, longitudinally extending interior space 112 formed by the wall of central portion 104. Space 112 communicates with the vacuum means of the invention, which here comprises a vacuum source such as vacuum pump "P" of standard construction (FIG. 16). Vacuum pump "P" is interconnected with space 112 by means of the previously mentioned vacuum supply 108, which here comprises tubular conduit having tubular end portion 108a. End portion 108a is adapted to be removably, telescopically received within tubular end portion 110b of wall 110 in the manner shown in FIG. 16. In a manner presently to be described, the vacuum pump creates a vacuum within tubular space 112 that is sufficient to capture and channel through space 112 both the cooling water and the grinding debris which is generated proximate the scoop portion 116 of housing 106 during the grinding drilling procedures.

Figure 19:
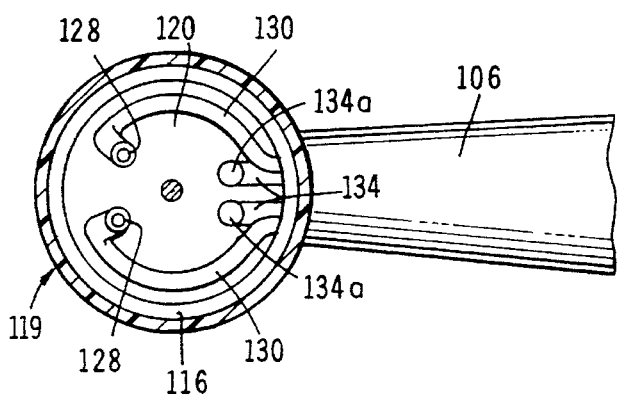
FIG. 19 is a cross-sectional view taken along lines 19—19 of FIG. 16.

In order to cool the work tool 122 as well as the work site, fluid cooling means are provided. The fluid cooling means here comprises a source of cooling fluid "W", which is preferably cool water. A pair of fluid spray jets 128 (FIG. 19) which are in communication with the source of cooling fluid, are mounted within scoop portion 116 of housing 106 for controllably directing the cooling water toward the work tool 122. Also comprising a part of the cooling means are water carrying conduits 130 which extend through housing 106 and, in a manner presently to be described, are connected by means of novel interconnection means to a second pair of water carrying conduits 132 which extend through hollow handle 104. Conduits 132 are, in turn, connected via novel connection means to third water carrying conduits that are appropriately interconnected with the source of cooling water "W".

Forming another important feature of the apparatus of the present invention is the provision of illumination means for illuminating the work site. This means here comprises a multiplicity of bundled together optic fibers 134 which extend through housing 106 and terminate at one end 134a at a location proximate the work site. The previously mentioned connector means of the invention functions not only to connect the cooling water conduits with the source of cooling water, but also functions to connect the gas conduit 124 and the optic fibers 134 to remotely located sources of gas and light respectively.

In the form of the invention shown in FIGS. 13 through 16, the connector means uniquely comprise an angularly extending, generally tubular shaped connector arm 140 which is integrally formed with hollow handle 104. The water conduits 132, as well as a second gas conduit 125, which is connected to gas conduit 124 via the interconnection means of the invention, are channeled through arm 140 and terminate in a connector disk assembly 142 which is telescopically received within the open end 140a of arm 140. Additionally, a second bundle of optic strands 136, which are interconnected to optic strands 134 via the interconnection means, are channeled through arm 140 and also terminate in connector disk assembly 142. As indicated in FIGS. 15 and 25, each of the water conduits, the gas conduit and the fiber optic strands terminate in female connector sockets 142a, which form a part of disk assembly 142 and which matably receive male connector members 132a, 136a and 125a which are provided on a second connector disk assembly 143 which also forms a part of the connector means. A third gas conduit 144 has one end connected to connector 125a in the manner illustrated in FIG. 16 and a second end connected to gas source "G". Similarly, third water carrying conduits 145 are connected at one end to connectors 132a while a third fiber bundle 146 is connected to connector 136a. The outboard ends of water conduits 144 are appropriately interconnected with the source of cooling water "W" while the outboard end of fiber bundle 146 is appropriately interconnected with the light source "L".

Turning next to FIGS. 13 and 16, it can be seen that connector disk 143 as well as conduits 144 and 145 and fiber bundle 146 are contained within a tubular supply encasement 150. A connector ring 152 in turn surrounds encasement 150 and, in the manner shown in FIG. 16, is adapted to be mated with a connector ring 154 which surrounds arm 140. A spring biased clip member 156, which is connected to ring 154, has a resilient locking tab 156a which, in addition to sockets 142a, functions to releasably interconnect disks 137 and 142 as the disks are moved into mating engagement in the manner shown in FIG. 16. More particularly, tab 156a is receivable within a cavity 143a formed in ring 143 and functions to releasably maintain disks 142 and 143 and functions to releasably maintain disks 142 and 143 in mating engagement. It is to be understood that various locking mechanisms of a character well known to those skilled in the art can be used to interconnect encasement 150 with arm 140.

Figure 20:
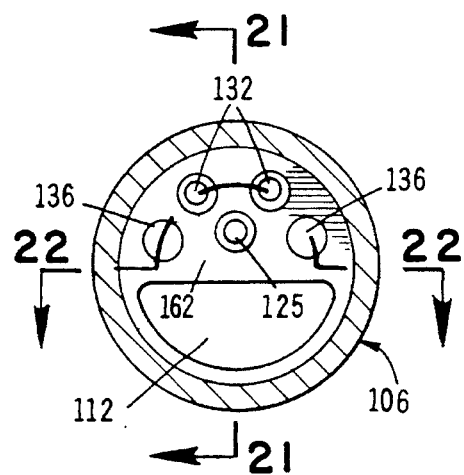
FIG. 20 is a view taken along lines 20—20 of Figure1 6.
Figure 21:
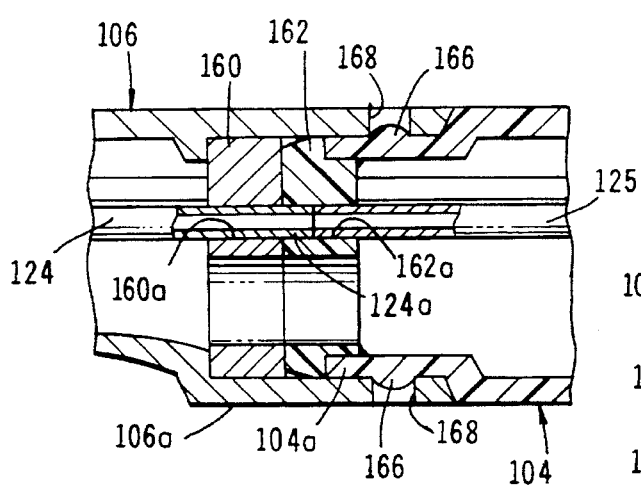
FIG. 21 is a cross-sectional view taken along lines 21—21 of FIG. 20.
Figure 22:
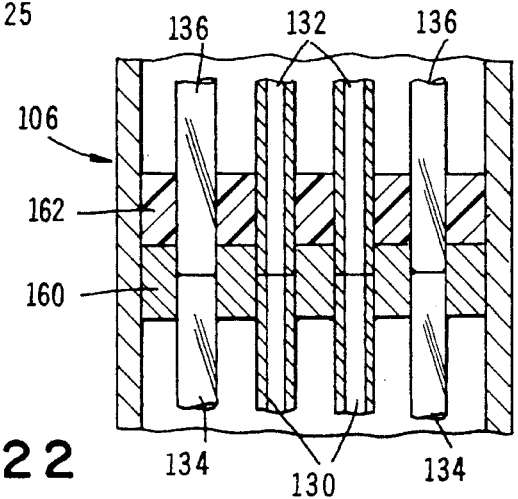
FIG. 22 is a cross-sectional view taken along lines 22—22 of FIG. 20.

Turning now to FIGS. 20, 21, and 22, the previously mentioned interconnection means of the invention for interconnecting together first and second water conduits 130 and 132 and for interconnecting together first and second gas conduits 124 and 125 is there illustrated. In the present form of the invention, the interconnection means also interconnects together first and second fiber optic bundles 134 and 136. The interconnection means here comprises first and second connector disks 160 and 162 which are secured together in mating engagement in the manner shown in FIGS. 21 and 22. More particularly, connector disk 160 is mounted within tubular end portion 106a of housing 106 while connector disk 162 is mounted within reduced diameter portion 104a of tubular handle 104. As best seen in FIG. 21, the outboard end 124a of gas conduit 124 extends through an aperture 160a provided in disk 160 and is, in turn, receivable within an indexable aperture 162a provided in disk 162. Conduit 125 terminates in an aperture 162a formed in disk 162 so that when the disks are moved into mating engagement, conductor 124 will communicate with conductor 125. As indicated in FIG. 22, conduits 130 and fiber bundles 134 strategically terminate in spaced-apart apertures formed in connector disk 160, while conduits 132 and fiber bundles 136 extend through indexable apertures formed in disk 162. With this construction, when disks 160 and 162 are moved into the mating relationship shown in FIG. 21, conduits 130 will operably communicate with conduits 132 while fiber bundles 134 will operably commuicate with fiber bundles 136. As disks 160 and 162 move into mating engagement, the reduced diameter portion 104a of handle 104 is telescopically received within tubular end portion 106a of housing 106 and is held in position therein by locking protuberances 166 which are formed on reduced diameter portion 104a. Protuberances 166 are lockably receivable within apertures 168 formed in portion 106a of housing 106 (FIG. 21).

It is apparent that when the hand piece is assembled in the manner shown in FIG. 16, gas conduit 124 is in communication with the compressed gas source "G" and water conduits 130 are in communication with the remotely located source of cooling water "W". Similarly, fiber optic bundles 134 are in communication with the remotely located source of light "L". Advantageously, however, with the unique construction described in the preceding paragraphs, disposable handle portion 104 of the device can be easily separated from housing 106, from vacuum supply conduit 108 and from encasement 150 so that, following the surgical procedure, it can be discarded and replaced with a new, sterile hollow handle portion.

Figure 18:
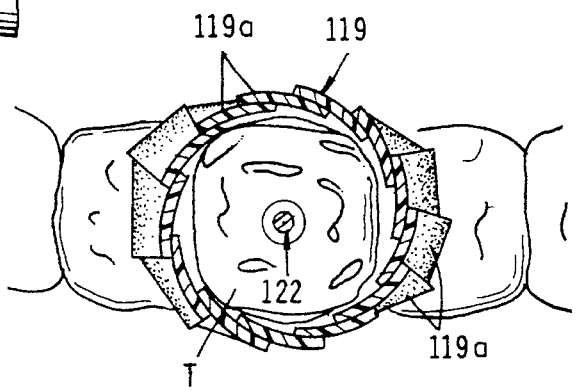
FIG. 18 is a cross-sectional view taken along lines 18—18 of FIG. 16.

Another highly novel feature of this latest form of the invention comprises the previously identified flexible shroud 119 which is connected to and depends from scoop portion 116 of housing 106. As best seen by referring to FIG. 18, shroud 119 is made up of a multiplicity of overlapping, clear plastic, flexible segments 119a that cooperate to form a skirt-like portion which, as illustrated in FIG. 16, circumscribes tooth "T" during the grinding operation. Because segments 119 are constructed of a flexible plastic material, they will readily conform to the shape of the tooth "T" and at the same time will uniquely function to channel cooling water, grinding debris and aerosols into scoop portion 118 of housing 106. More particularly, when handle 104 is interconnected with a source of vacuum in the manner shown in FIG. 16, energization of the vacuum pump "P" will and cause the water and grinding debris to be efficiently sucked into interior space 112 of the handle portion and then into the vacuum supply tube 108 for capture and safe disposition.

Shroud assembly 119, like handle 104, is readily disposable. In this regard, as shown in FIG. 12, shroud 119 is provided with an upstanding connector portion 119b which is arcuately shaped in cross section so that it can be closely fitted around the forward wall 107 of housing 106 and securely maintained in position due to its frictional engagement with wall 107.

As was the case with the earlier described embodiment of the invention, working tool 122 can be expediciously connected and disconnected to the pneumatic motor by chuck operating lever means of a character well known by those skilled in the art and generally designated in FIGS. 14 and 17 by the numeral 160.

In using the apparatus of the invention, a fresh, unused sterile handle portion 104 is first mated with housing 106 through use of the interconnection means of the invention. Next, encasement 150 which houses the gas and water supply conduits and the fiber optic bundle 146, is mated with connector arm 140 in the manner shown in FIGS. 15 and 16. Finally, the vacuum supply tube 108 is telescopically inserted into end 110a of handle portion 104 so that upon energization of the vacuum pump, a vacuum will be created in the area of scoop portion 118 of housing 106.

In performing the surgical procedure and with the vacuum pump energized, with gas flowing to motor 120, and with the fiber bundles illuminated, the user grasps handle 104 proximate the corrugated central portion 104a thereof and brings working tool 122 into working engagement with the tooth "T". As the tool moves into engagement with the tooth, shroud 119 will closely circumscribe the tooth in the manner shown in FIG. 16 causing the cooling water and the grinding debris entrained therewithin to be efficiently channeled into scoop 118 and then carried into interior space 112 of the handle portion. To enable precise positioning of the working tool relative to the tooth, the central portion of handle 104 is swiveled between a pair of longitudinally spaced swivel rings 177. Swivel rings 177 are of a standard well-known construction and permit relative rotation between the central portion of handle 104 and the distal and proximal portions thereof.

During the grinding procedure, cooling water is, of course, flowing from jets 128 and the work area is being appropriately illuminated by light from the fiber optic bundles 134. As before, since the water and debris is being expeditiously carried away from the tooth during the grinding operation, no need exists for a dental assistant to remove the water and debris in a conventional manner using auxiliary suction devices. To appropriately control the amount of suctionbeing exerted during the grinding operation, a valve assembly "V" (FIG. 16) of well-known construction is provided within vacuum supply tube 108 and is operable in a conventional manner by means of a valve handle V-1 which extends through an opening formed in the wall of member 108.

Turning to FIGS. 23 through 27, still another form of aspirating hand piece of the invention is there shown. This embodiment is similar in many respects to the embodiment shown in FIGS. 13 through 22 and like numbers are used to identify like components. However, in this latest form of the invention, the central handle portion 204 and the intake means, including housing 206, are integrally formed from a suitable metal such as stainless steel.

As before, central portion 204 includes an outer wall 210 which defines a longitudinally extending interior space 212. As best seen in FIG. 25, proximal end 210b of the handle terminates in a tubular portion which is adapted to telescopically receive a reduced diameter portion 208a of flexible vacuum supply hose 208.

Turning particularly to FIGS. 23 and 25, it is to be observed that housing 206 terminates proximate one end in a downwardly depending scoop-like portion 216 having an open mouth 218. A gas driven motor 120, which is carried within housing 106, is adapted to rotatably drive the work tool 122 which extends outwardly from mouth 218 for engagement with the work site such as a tooth "T". Motor 120 is driven in conventional fashion by a compressed gas, such as compressed air, which is carried by a gas conduit 224 which, as before, is in communication with a remotely located source of compressed gas "G". The motor is exhausted into space 212 aiding in the aspiration of the device via a venturi effect.

Space 212 of the assembly communicates with the vacuum means of the invention which, as before, comprises a vacuum source such as vacuum pump. The vacuum pump is interconnected with space 212 by means of the vacuum supply tube 208 and creates a vacuum within interior space 212 that is sufficient to capture and channel through space 212 both the cooling water, aerosols and the grinding debris which is generated during the grinding drilling procedures.

In this latest form of the invention and also in the form of the invention shown in FIGS. 13 through 22, the vacuum pump and the aspirating orifices are uniquely sized to the hand piece and will aspirate between approximately ten and thirty cubic feet per minute (CFM) of air and approximately 0.2 to 0.6 CFM of fluid. In this way, the aspiration will not be adversely affected by accumulation of particulate matter.

A pair of fluid spay jets 128, which are in communication with a source of cooling fluid, are mounted within scoop portion 216 of housing 206 for controllably directing the cooling water toward the work tool 122. Also comprising a part of the cooling means are water carrying conduits 230 which extend through the assembly and are, in turn, connected via the connection means to water carrying conduits 144 that are appropriately interconnected with the source of cooling water.

As in the earlier described embodiments, the apparatus of the present invention includes illumination means for illuminating the work site. This means here comprises a multiplicity of bundled together optic fibers 234 which extend through housing 206 and terminate at a location proximate the work site. The previously mentioned connector means of the invention functions not only to interconnect the cooling water conduits with the source of cooling water, but also functions to interconnect the gas conduit 224 and the optic fibers 234 with remotely located sources of gas and light respectively. The connector means of the form of the invention shown in FIGS. 23 through 27 is identical to the connector means of FIGS. 13 through 16 and will not be further described, save to say that the connector arm 240 which is integrally formed with hollow handle 204 is constructed of metal rather than plastic.

The water conduits 230 as well as gas conduit 224 are channeled through arm 240 and terminate in connector disk 142 which is connected to open end 240a of arm 240 in the manner shown in FIG. 25. Additionally, optic strands 234 are channeled through arm 240 and terminate in connector disk 142. As before, the outboard ends of water conduits 145 are appropriately interconnected with the source of cooling water "W", while the outboard end of fiber bundle 146 is appropriately interconnected with the light source "L". Similarly, the outboard end of gas conduit 144 is connected with a source of compressed gas in the manner previously described herein. Connector disk 143 as well as conduits 144 and 145 and fiber bundle 146 are, as before, surrounded by a tubular supply encasement 150.

When the hand piece is assembled in the manner shown in FIG. 25, gas conduit 224 is in communication, via the connector means, with the compressed gas source "G" and water conduits 230 are in communication via the connector means with the remotely located source of cooling water "W". Similarly, fiber optic bundle 234 is in communication via the connector means with the remotely located source of light "L". Advantageously, however, handle portion 204 of the device can be easily separated from vacuum supply conduit 208 and from encasement 150 so that, following the surgical procedure, it can be appropriately sterilized.

This latest form of the invention also comprises the previously identified flexible shroud 119 which is connected to and depends from scoop portion 216 of housing 206. As before, shroud 119 is made up of a multiplicity of overlapping flexible segments 119a that cooperate to form a shirt-like portion which, as illustrated in FIG. 25, circumscribes tooth "T" during the grinding operation.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A hand piece for use in performing surgical and dental procedures including a rotatable work tool, said work tool being cooled by water from an external source of water, said hand piece comprising:
   (a) an elongated handle assembly, including a hollow handle having a distal end, a proximal end and an outer wall defining an interior space, said handle assembly further comprising:
      (i) a cooling water conduit disposed within said interior space of said hollow handle; and
      (ii) connector means disposed intermediate said distal end and said proximal end of said hollow handle for interconnecting said cooling water conduit with the external source of water;
   (b) intake means disposed proximate the work tool and in communication with said interior space of said hollow housing of said handle assembly for capturing the cooling water and channeling it into said interior space said intake means comprising a downwardly depending scoop partially surrounding the work tool, said scoop having side walls defining an open mouth for capturing debris generated by the action of the work tool and for channeling the debris along with the cooling water into said interior space;
   (c) vacuum means connected to said proximal end of said hollow handle for creating a vacuum at said intake means.

2. A hand piece as defined in claim 1 further including at least one fluid spray jet mounted within said scoop on the distal side of the work tool, said fluid spray jet being connected to said cooling water conduit.

3. A hand piece as defined in claim 1 in which said hollow handle includes an internal dividing wall connected to said outer wall for dividing said interior space into first and second portion, said cooling water conduit being disposed within said first portion and said vacuum means creating a vacuum within said second portion.

4. A hand piece as defined in claim 1 in which said intake means further includes a downwardly depending, flexible shroud connected to said scoop for substantially surrounding the work tool.

5. A hand piece for use in performing surgical and dental procedures including a rotatable work tool, said work tool being cooled by water from an external source of water, said hand piece comprising:
   (a) an elongated handle assembly, including a hollow handle having a distal end, a proximal end and an outer wall defining an interior space, said handle assembly further comprising:
      (i) a cooling water conduit disposed within said interior space of said hollow handle; and
      (ii) connector means disposed intermediate said distal end and said proximal end of said hollow handle for interconnecting said cooling water conduit with the external source of water;
   (b) intake means disposed proximate the work tool and in communication with said interior space of said hollow housing of said handle assembly for capturing the cooling water and channeling it into said interior space, said intake means comprising:
      (i) a housing having first and second end portions, said first end portion being removably interconnected with said distal end of said hollow handle;
      (ii) a gas driven motor mounted within said housing for rotating the work tool; and
      (iii) a flexible shroud connected to said second end portion of said housing and circumscribing the rotatable work tool.

6. A hand piece as defined in claim 5 in which said handle assembly further comprises a gas conduit disposed within said interior space of said hollow handle, said connector means being adapted to interconnect said gas conduit with an external source of gas.

7. A dental hand piece as defined in claim 5 further including illumination means for illuminating an area proximate said work tool, said illumination means comprising a multiplicity of optical fibers disposed within said interior space of said hollow handle.

8. A dental hand piece as defined in claim 7 in which said connector means is adapted to interconnect said optical fibers with an external source of light.

9. A hand piece for use in performing surgical and dental procedures, including a rotatable work tool, said work tool being cooled by water from an external source of water, said hand piece comprising:
   (a) an elongated handle assembly, including a hollow handle having a distal end, a tubular shaped proximal end and an outer wall defining an interior space, said handle assembly further comprising:
      (i) a cooling water conduit disposed within said interior space;
      (ii) a gas conduit disposed within said interior space; and
      (iii) a connector means disposed intermediate said distal end and said proximal end of said hollow handle for interconnecting said cooling water conduit with the external source of water and for interconnecting said gas conduit with an external source of gas, said connector means comprising:

a. an angularly extending connector arm integrally formed with said hollow handle at a location intermediate said proximal and distal ends thereof; and b. a first connector disk mounted within said connector arm, said cooling water conduit and said gas conduit being connected to said first connector disk;

(b) intake means, including a hollow housing connected to said hollow handle proximate said distal end thereof, said intake means communicating with said interior space of said hollow handle for capturing a substantial portion of the cooling water and channeling it into said interior space of said hollow housing; and (c) vacuum means connected to said proximal end of said hollow handle for creating a vacuum at said intake means, said vacuum means comprising a tubular member having a first end telescopically receivable within said proximal end of said elongated hollow handle member.

10. A hand piece as defined in claim 9 in which said connector means further comprises:

(a) a second connector disk for matable engagement with said first connector disk;

(b) a second gas conduit having a first end connected to said second connector disk and a second end connected to the external source of gas; and (c) a second water conduit having a first end connected to said second connector disk and a second end connected to the external source of water.

11. A hand piece as defined in claim 9 further including interconnection means for removably interconnecting said hollow housing of said intake means with said hollow handle.

12. A hand piece as defined in claim 9 in which said intake means further includes a flexible shroud connected to said housing and at least partially circumscribing the work tool.

13. A hand piece as defined in claim 12 in which said flexible shroud comprises a multiplicity of downwardly depending, overlapping flexible segments connected to said housing of said intake means.

14. A hand piece as defined in claim 13 in which said flexible shroud further comprises means for removably connecting said shroud to said housing of said intake means.

15. A hand piece for use in performing surgical and dental procedures, including a rotatable work tool, said work tool being cooled by water from an external source of water, said hand piece comprising:

(a) an elongated, handle assembly, including a disposable hollow handle having a distal end, a tubular shaped proximal end and an outer wall defining an interior space, said handle assembly further comprising:
  (i) a cooling water conduit disposed within said interior space;
  (ii) a gas conduit disposed within said interior space;
  (iii) a bundle of optical fibers disposed within said interior space; and
  (iv) a connector for interconnecting said bundle of optical fibers with a source of light, for interconnecting said cooling water conduit with the external source of water and for interconnecting said gas conduit with an external source of gas, said connector means comprising a connector arm connected to said hollow handle at a location intermediate its ends, said connector means comprising:
    a. a first connector disk mounted within said connector arm, said cooling water conduit, said gas conduit and said bundle of optical fibers being connected thereto;
    b. a second connector disk removably interconnected with said first connector disk;
    c. a second gas conduit having a first end connected to said second connector disk and a second end connected to the external source of gas;
    d. a second water conduit having a first end connected to said second connector disk and a second end connected to the external source of water; and
    e. a second bundle of optical fibers having a first end connected to said second connector disk and a second end connected to an external source of light;

(b) intake means, including a hollow housing removably connected to said hollow handle proximate said distal end thereof, said intake means communicating with said interior space of said hollow handle for capturing a substantial portion of the cooling water and channeling it into said interior space of said hollow housing; and (c) vacuum means removably connected to said proximal end of said hollow handle for creating a vacuum at said intake means, said vacuum means comprising a tubular member having a first end removably receivable within said proximal end of said disposable hollow handle member.

16. A hand piece for use in performing surgical and dental procedures, including a rotatable work tool, said work tool being cooled by water from an external source of water, said hand piece comprising:

(a) an elongated handle assembly, including a disposable hollow handle having a distal end, a proximal end and an outer wall defining an interior space, said handle assembly further comprising:
  (i) a cooling water conduit disposed within said interior space;
  (ii) a gas conduit disposed within said interior space;
  (iii) a bundle of optical fibers disposed within said interior space; and
  (iv) a connector for interconnecting said bundle of optical fibers with a source of light, for interconnecting said cooling water conduit with the external source of water and for interconnecting said gas conduit with an external source of gas, said connector means comprising a connector arm connected to said hollow handle at a location intermediate its ends;

(b) intake means, including a hollow housing removably connected to said hollow handle proximate said distal end thereof, said intake means communicating with said interior space of said hollow handle for capturing a substantial portion of the cooling water and channeling it into said interior space of said hollow housing said intake means further including a flexible shroud connected to said housing and at least partially circumscribing the work tool; and (c) vacuum means removable connected to said proximal end of said hollow handle for creating a vacuum at said intake means.

17. A hand piece for use in performing surgical and dental procedures, including a rotatable work tool, said work tool being cooled by water from an external source of water, said hand piece comprising:

(a) an elongated handle assembly, including a disposable, flexible plastic hollow handle having a distal end, a proximal end and an outer wall defining an interior space, said handle assembly further comprising:
(i) a cooling water conduit disposed within said interior space;
(ii) a gas conduit disposed within said interior space;
(iii) a bundle of optical fibers disposed within said interior space; and
(iv) a connector for interconnecting said bundle of optical fibers with a source of light, for interconnecting said cooling water conduit with the external source of water and for interconnecting said gas conduit with an external source of gas, said connector means comprising a connector arm connected to said hollow handle at a location intermediate its ends;
(b) intake means, including a hollow housing removably connected to said hollow handle proximate said distal end thereof, said intake means communicating with said interior space of said hollow handle for capturing a substantial portion of the cooling water and channeling it into said interior space of said hollow housing;
(c) vacuum means removably connected to said proximal end of said hollow handle for creating a vacuum at said intake means.

18. A hand piece for use in performing surgical and dental procedures, including a rotatable work tool, said work tool being cooled by water from an external source of water, said hand piece comprising:

(a) an elongated handle assembly, including a disposable, hollow handle having a distal end, a proximal end and an outer wall defining an interior space, said handle assembly further comprising:
(i) a cooling water conduit disposed within said interior space;
(ii) a gas conduit disposed within said interior space; and
(iii) a connector for interconnecting said cooling water conduit with the external source of water and for interconnecting said gas conduit with an external source of gas;
(b) intake means, including a hollow housing having a downwardly depending shroud removably connected to said hollow handle proximate said distal end thereof, said intake means communicating with said interior space of said hollow handle for capturing a substantial portion of the cooling water and channeling it into said interior space of said hollow housing;
(c) interconnection means for removably interconnecting said hollow housing of said intake means with said hollow handle; and
(d) vacuum means removably connected to said proximal end of said hollow handle for creating a vacuum at said intake means.

\* \* \* \* \*